United States Patent [19]

Hueil et al.

[11] 4,043,504

[45] Aug. 23, 1977

[54] STAPLE CARTRIDGE AND FEED MEANS FOR USE WITH A SURGICAL STAPLING INSTRUMENT

[75] Inventors: J. Charles Hueil, Loveland, Ohio; Robert G. Rothfuss, Bellevue, Ky.

[73] Assignee: Senco Products, Inc., Cincinnati, Ohio

[21] Appl. No.: 665,294

[22] Filed: Mar. 9, 1976

[51] Int. Cl.² .............................................. B25C 5/02
[52] U.S. Cl. ..................................... 227/116; 227/19; 227/120
[58] Field of Search .................... 227/19, 85, 95, 114, 227/116, 120, 126

[56] References Cited

U.S. PATENT DOCUMENTS

| | | | |
|---|---|---|---|
| 2,178,354 | 10/1939 | Brownstein | 227/126 |
| 2,231,539 | 2/1941 | Larsen | 227/116 |
| 2,240,455 | 4/1941 | Carlile | 227/95 |
| 2,632,889 | 3/1953 | Beecroft | 227/120 |
| 3,638,847 | 2/1972 | Noiles et al. | 227/120 |
| 3,873,016 | 3/1975 | Fishbein | 227/19 |

*Primary Examiner*—Granville Y. Custer, Jr.
*Attorney, Agent, or Firm*—Melville, Strasser, Foster & Hoffman

[57] ABSTRACT

A staple cartridge and feed means for use with a surgical stapling instrument of the type having an anvil about which a staple is formed during emplacement thereof in the skin or fascia of a patient. The cartridge comprises a body having a vertical staple feeding track adapted to hold a stack of staples and a separate vertical staple forming track with a staple former reciprocable therein by the surgical stapling instrument. The staple forming track and the staple feeding track are in parallel relationship separated by a divider wall. A window, defined by the cartridge body and the divider wall, provides a horizontal path between the staple feeding track and the staple forming track and is so sized as to permit the passage therethrough of a single staple from the bottom of the staple stack. Horizontal feeder means normally prevent passage of the bottommost staple from the stack through the window into the staple driving track. The horizontal feeder means, actuable by the surgical stapling instrument, positively shifts the bottommost staple of the stack from the staple feeding track horizontally through the window to the staple forming track and cooperates with retainer springs to hold a shifted staple in position in the staple forming track to be implanted and formed about the anvil by the staple former.

17 Claims, 16 Drawing Figures

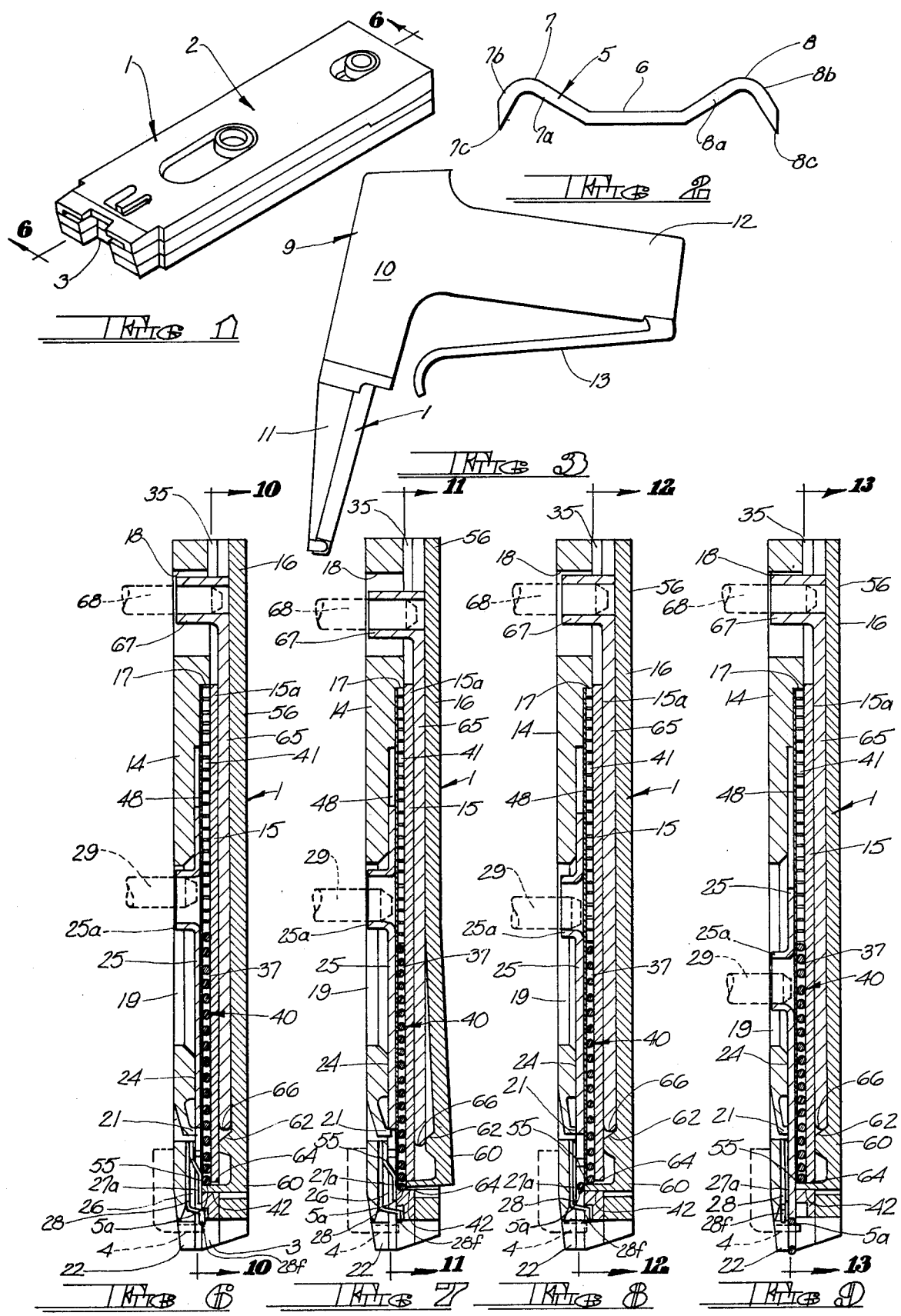

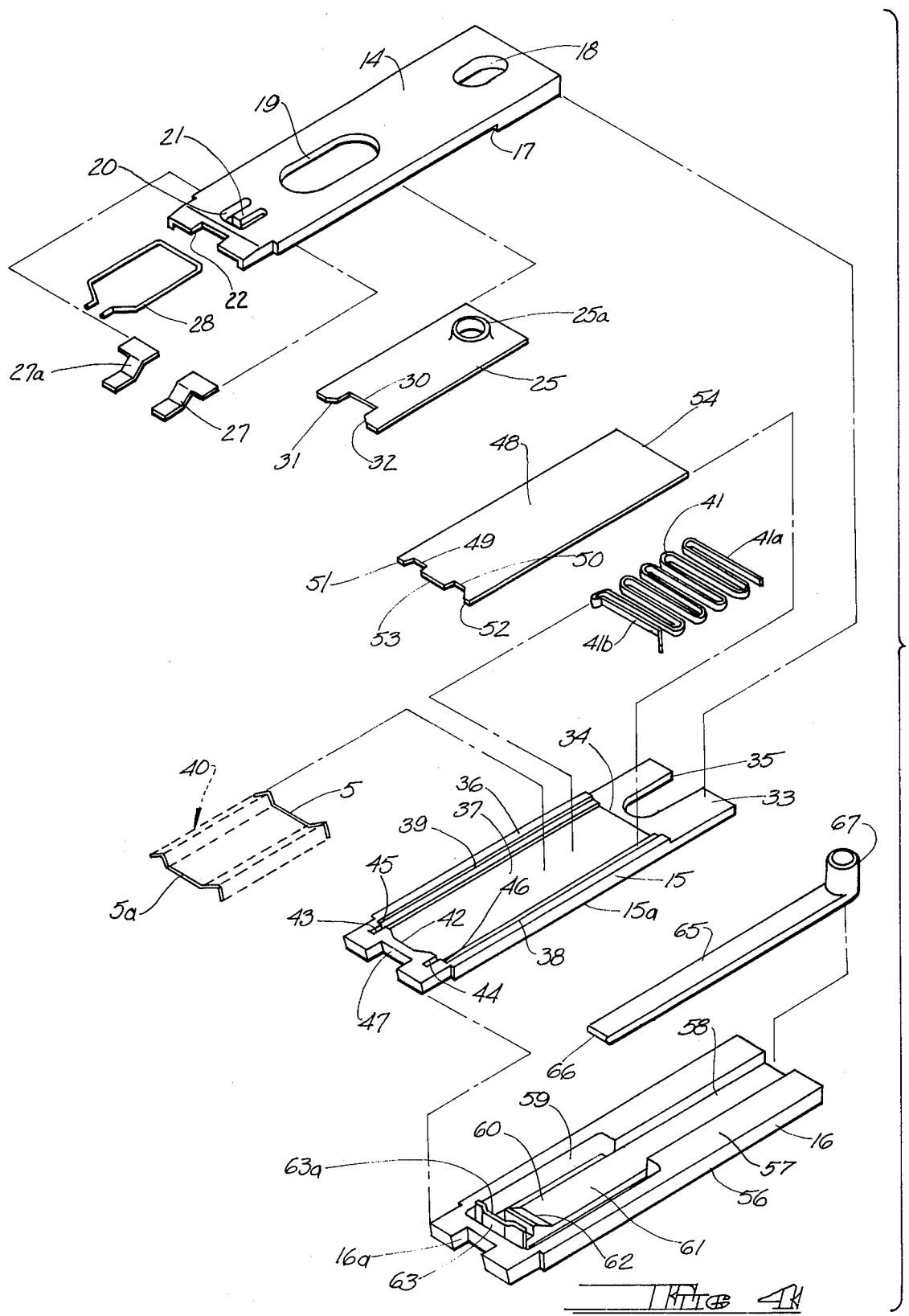

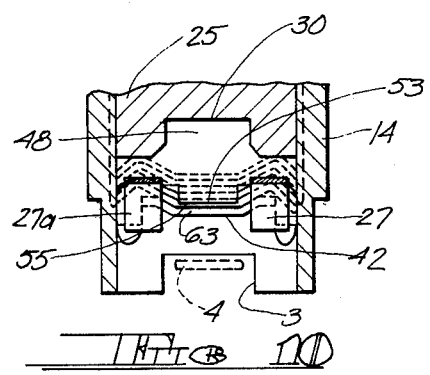
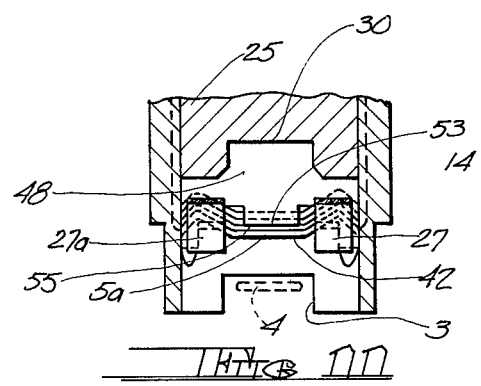
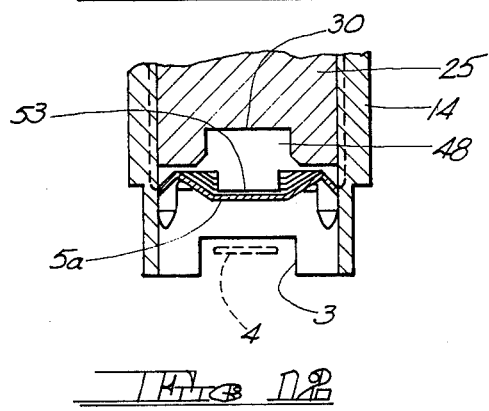
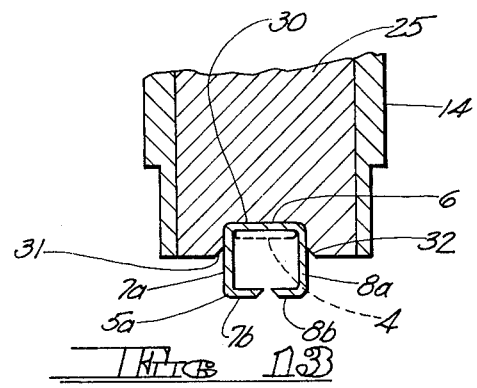
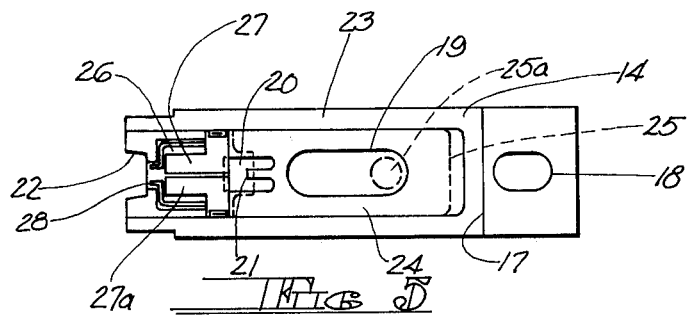
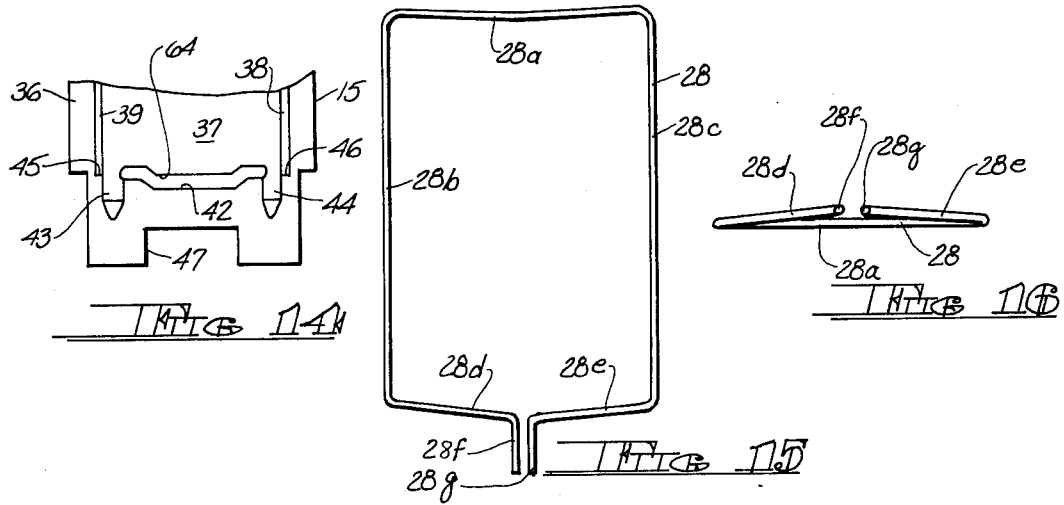

STAPLE CARTRIDGE AND FEED MEANS FOR USE WITH A SURGICAL STAPLING INSTRUMENT

BACKGROUND OF THE INVENTION

I. Field of the Invention

The invention relates to a staple cartridge and feed means and more particularly to a staple cartridge well suited for use with a surgical stapling instrument.

II. Description of the Prior Art

While the staple cartridge and feed means of the present invention is capable of many applications, it will, for purposes of an exemplary showing, be described in terms of its use with a surgical stapling instrument for which it is particularly well adapted. Recently, surgeons have come more and more to the use of staples, rather than conventional thread sutures, for closing wounds or incisions in the skin and fascia of a patient. This trend is due largely to the fact that the use of staples is a far easier procedure and, of even greater importance, is very much faster. This substantially reduces the time required for suturing and the length of time the patient must be maintained under anaesthesia.

Prior art workers have developed various types of surgical stapling instruments and staple cartridges for use therewith. Of particular concern has been the staple feed means within a cartridge and numerous approaches have been taken by prior art workers. For example, cartridges have been devised wherein the staple feed means comprises a pair of staple-advancing screws. The staples are retained by and advanced by the threads of the pair of staple-advancing screws and it will be appreciated that the pair of screws must be turned very precisely to prevent jamming of the staples within the cartridge. As a consequence, complex gear means or cam means are required to turn the staple-advancing screws. Examples of such cartridges are taught in U.S. Pat. Nos. 3,618,842 and 3,643,851.

Another approach is taught in U.S. Pat. No. 3,638,847 wherein the cartridge is provided with a stationary sawtooth staple-retaining member and a reciprocating sawtooth staple advancing member adapted to cooperate with the staple former or pusher. U.S. Pat. No. 3,650,453; 3,717,294 and 3,837,555 teach yet another approach wherein a plurality of staples are guided and advanced by a continuous belt adapted for rotation within the cartridge. The belt and staples mounted thereon are advanced by the action of the staple former or by the inter-action of the staple former and the forwardmost staple.

It will be evident from the foregoing that prior art staple cartridge and feed means have been complex in construction and difficult and expensive to manufacture. The complexity of the feed means has had a direct bearing on the reliability of prior art cartridges, it being understood by one skilled in the art that once a staple has jammed within the cartridge, the cartridge and its remaining staples cannot be further used. The complexity of prior art staple cartridge and feed means has been reflected in the complexity and expense of the surgical stapling instruments with which the cartridges are used. The use of complicated gear means or the staple former itself to advance the staples within the cartridge has required considerable power from the surgical stapling instrument.

The present invention is based upon the discovery that a very much simpler, less expensive, and more reliable staple cartridge can be achieved by providing a vertical staple feeding track to accommodate a plurality of staples and spring means to advance the staples therein; a separate vertical, parallel staple forming track housing a reciprocating staple former; a window providing a horizontal passage between the two tracks and sized to permit a single staple to pass therethrough; means to normally maintain the staples within the staple feeding track; positive means to selectively shift a single staple from the staple feeding track through the window to the staple forming track and means to maintain such a shifted staple in proper position within the staple forming track for engagement by the staple former. The provision of vertical staple feed means and horizontal staple feed means which are independent of each other and independent of the staple former results in an arrangement in which the staples are far less likely to become jammed. In this arrangement the staple feeding portion of the cartridge cycle is completed before the start of the staple forming portion of the cartridge cycle.

The cartridge of the present invention requires less power from the surgical staple instrument to operate it. The staple feeding means is extremely reliable with the result that staples can be consistently and accurately formed about the anvil of the surgical stapling instrument.

SUMMARY OF THE INVENTION

The staple cartridge and feed means of the present invention comprises an elongated body having separate, parallel, vertical staple feeding and staple forming tracks. These tracks are separated from each other by a thin divider wall. The staple feeding track is adapted to accommodate a stack of staples and a feeder spring to advance the staples along the staple feeding track. The staple forming track has a staple former slidably mounted therein and shiftable between retracted and extended positions by the surgical stapling instrument with which the cartridge is used.

A window defined by the cartridge body and the divider wall provides a horizontal passage between the staple feeding track and the staple forming track. This window is so sized and configured as to permit the passage therethrough of only one staple at a time (i.e. the bottommost staple of the staple stack).

A positive horizontal feeder means, actuable by the surgical stapling instrument, is provided to shift the bottommost staple of the staple stack through the window and into the staple forming track. Retainer springs are located in the staple forming track. These retainer springs cooperate with the window and the horizontal feeder to permit the passage of only single staples through the window. The positive horizontal feeder means and the window cooperate to retain the remainder of the staple supply within the staple feeding track. The retainer springs additionally cooperate with the horizontal feeder and staple former to maintain a staple, having been shifted through the window, in proper position within the staple forming track for engagement by the staple former. The cartridge may also be provided with a staple ejection spring to assist in removal of a formed staple from the anvil of the surgical stapling instrument.

As will be described hereinafter, the staple cartridge and feed means of the present invention may be so dimensioned as to accommodate staples of any desired size and suitable configuration and can be made to be disposable or refillable and reusable.

BRIEF DESCRIPTION OF THE DRAWINGS

FIG. 1 is a perspective view of the staple cartridge and feed means of the present invention.

FIG. 2 is a front elevational view of a staple usable in the cartridge of the present invention.

FIG. 3 is a semi-diagrammatic side elevational view of a surgical stapling instrument with the cartridge mounted thereon.

FIG. 4 is an exploded perspective view of the staple cartridge and feed means of the present invention illustrating the components thereof.

FIG. 5 is a plan view of that side of the staple former housing not shown in FIG. 4.

FIG. 6 is a cross-sectional view taken along section line 6—6 of FIG. 1 and illustrates the components of the staple cartridge and feed means in their normal, at rest positions.

FIG. 7 is a cross-sectional view similar to FIG. 5 with the components of the staple cartridge and feed means in their respective positions when the horizontal feeder is in its most retracted position.

FIG. 8 is a cross-sectional view similar to FIGS. 6 and 7 with the components of the staple cartridge and feed means in their respective positions immediately after the horizontal feeding of a staple through the window has been accomplished.

FIG. 9 is a cross-sectional view similar to FIGS. 6 through 8 with the components of the staple cartridge and feed means in their respective positions when the staple has been formed about the anvil of the surgical stapling instrument.

FIG. 10 is a fragmentary cross-sectional view taken along section line 10—10 of FIG. 6.

FIG. 11 is a fragmentary cross-sectional view taken along section line 11—11 of FIG. 7. FIG. 12 is a fragmentary cross-sectional view taken along section line 12—12 of FIG. 8.

FIG. 13 is a fragmentary cross-sectional view taken along section line 13—13 of FIG. 9.

FIG. 14 is a fragmentary elevational view of the staple housing.

FIG. 15 is an elevational view of the staple ejection spring.

FIG. 16 is an end view of the staple ejection spring of FIG. 15 as seen from the bottom thereof.

DESCRIPTION OF THE PREFERRED EMBODIMENTS

FIG. 1 is a perspective view of the staple cartridge and feed means of the present invention. The cartridge is generally indicated at 1 and comprises an elongated, substantially rectangular body, generally indicated at 2. The bottom end of the cartridge is bifurcated, as shown at 3, to enable it to straddle the anvil 4 of the surgical instrument (see FIGS. 6 through 13). The staple cartridge and feed means of the present invention may be configured and dimensioned to accept various sizes and types of staples. While not intended to constitute a limitation on the present invention, for purposes of an exemplary showing the cartridge is illustrated and described as housing surgical staples of the type taught in the co-pending application Ser. No. 858,804, filed June 11, 1975 in the name of Robert G. Rothfuss and entitled: SURGICAL STAPLE.

A staple of the type taught in this co-pending application is illustrated in FIG. 2 and is generally indicated at 5. The staple comprises a crown portion 6 having legs 7 and 8. Legs 7 and 8 have first upwardly and outwardly sloping portions 7a and 8a terminating in second, downwardly and outwardly sloping portions 7b and 8b. The staple points 7c and 8c are formed by diagonal cuts across the leg ends. As is explained in the above identified co-pending application the cuts forming points 7c and 8c are so arranged as to be perpendicular to the upper surface of the surgical stapling instrument anvil 4 and the skin or fascia of the patient, whereby the staple penetrates the skin or fascia during emplacement without the tendency to slide therealong. The configuration of this staple not only affords greater skin gathering during emplacement, but also facilitates stacking of the staples in the cartridge staple feeding track, allowing more staples per linear inch of staple feeding track.

FIG. 3 illustrates in semi-diagrammatic fashion a surgical stapling tool generally indicated at 9. The tool comprises a body 10 having a nose portion 11, a handle portion 12 and an actuator or trigger 13. The cartridge 1 is shown in place on the nose 11 of the instrument. The precise configuration and the operating instrumentalities of the surgical stapling instrument do not constitute limitations of the present invention. The device may be fluid powered, mechanically actuated by trigger 13, or the like. It will be understood by one skilled in the art that the anvil 4 of the surgical instrument 9 is located at the free end of nose 11, although not visible in FIG. 3.

For a better understanding of the staple cartridge and feeding means of the present invention reference is now made to FIGS. 4 and 6 wherein like parts have been given like index numerals. The body 2 of the cartridge 1 of FIG. 1 is made up of three basic parts between which all of the remaining parts are located. These basic parts comprise a staple former housing 14, a staple housing 15 and a horizontal feeder housing 16. The parts 14 through 16 may be made of any suitable material approved for use in a surgical environment and capable of withstanding sterilization procedures. While not so limited, stainless steel may be used for parts 14 through 16, particularly when the cartridge is intended to be refillable and reusable. Under these circumstances, these parts may be joined together by screws or other removable fastening means. When the cartridge is intended to be disposable these parts are preferably made of plastic or the like. The parts 14 through 16 lend themselves well to be molded from a plastic material suitable for surgical use. Under these circumstances the parts 14 through 16 may be joined together by ultrasonic welding, gluing or the like.

The staple former housing 14 has a planar exterior surface. The upper end of the staple former housing is of greater thickness than the remainder thereof, forming a shoulder 17. A perforation 18 of elongated configuration passes through the upper portion. The intermediate portion of the staple former housing has a second perforation 19 pssing therethrough. The perforation 19 is of greater length than perforation 18. Yet another perforation 20 passes through the staple former housing and is of U-shaped configuration defining an integral, resilient tine or foot 21 which serves as a staple former detainer, as will be described hereinafter. The bottommost end of the staple former housing has a notch 22 within which the anvil 4 of the surgical stapling instrument 9 is received and forming a part of notch 3 of FIG. 1. Turning to FIG. 5, it will be noted that the interior surface of that portion of the staple former housing 14 to the left of shoulder 17 (as viewed in FIG. 5) comprises a planar, U-shaped surface 23 surrounding a longitudinal depression 24 adapted to receive the staple former 25 shown in broken lines. The depression 24 extends all the way to the bottom end of the staple former housing 14 and constitutes the staple former track of the cartridge within which the staple former 25 may shift between a fully retracted position shown in FIG. 5 and a fully extended position (shown in FIG. 13) wherein the bottom edge of the staple former 25 extends to a position sufficient to accomplish forming of a staple. In the particular exemplary embodiment illustrated, the staple former travels all the way to the bottom edge of the staple former housing when in its fully extended position.

An additional depression 26 is located in the staple forming track 24 and is adapted to receive a pair of L-shaped retainer springs 27 and 27a which are staked, glued or otherwise appropriately attached to the staple former housing 14. As is most clearly shown in FIG. 6, that portion of depression 26 receiving the long legs of retainer springs 27 and 27a slopes downwardly and toward the exterior surface of the staple former housing 14. The purpose for this will be explained hereinafter. Retainer springs 27 and 27a are also clearly shown in FIG. 4. If desired, retainer springs 27 and 27a may be formed as an integral one-piece structure.

Beneath springs 27 and 27a there is positioned and attached to staple former housing 14 a staple ejection spring 28. Staple ejection spring 28 is optional but its presence is preferred to eject a formed staple from the anvil 4. Thus, staple ejection spring 28 aids the disconnection of the surgical stapling tool 9 from a staple formed around its anvil 4 and into the skin of the patient with a minimum of tramma to the patient.

Staple ejection spring 28 is most clearly shown in FIGS. 15 and 16 and is preferably made of roundwire spring tempered stainless steel or the like. Staple ejection spring 28 is formed into a near rectangle having a top 28a and sides 28b and 28c terminating in inturned legs 28d and 28e with downwardly depending tabs 28f and 28g. As is evident from FIG. 16, legs 28d and 28e are bent slightly out of the plane in which top 28a and sides 28b and 28c lie.

When staple ejection spring 28 is in its normal position (see FIG. 6) the spring legs 28d and 28c extend across the staple former track 24 with spring tabs 28f and 28g being located just above the top surface of anvil 4 at the free end of the anvil. Spring tab 28f is shown in FIG. 6. The operation of staple ejection spring 28 will be described hereinafter.

Turning again to FIG. 4 the staple former 25 constitutes a substantially rectangular, planar element having an upstanding driving eyelet 25a adapted to extend through the elongated perforation 19 of the staple former housing 14 and to be engaged by a drive pin 29 (shown in broken lines in FIGS. 6 through 9) of the surgical stapling instrument 9. The bottommost edge of staple former 25 has a notch 30 therein. The bottom corners of notch 30 are relieved as at 31 and 32. This configuration of the notch enables the staple former 25 to form a staple about the surgical stapling instrument anvil 4, as is illustrated in FIG. 13.

The staple housing 15 (FIGS. 4, 6 and 14) has a substantially planar surface 15a facing in the direction of the horizontal feeder housing 16. The upper end 33 of the staple housing 15 is of lesser thickness than the remainder of the staple housing, forming a shoulder 34. This upper end 33 is provided with an elongated, U-shaped notch 35, the purpose of which will be described hereinafter.

To the left of shoulder 34 (as viewed in FIG. 4) a planar surface 36 extends about three sides of a longitudinal depression 37 and a pair of flanking shoulders 38 and 39. The elongated depression 37 constitutes the staple feeding track of the cartridge and is intended to receive a stack (generally indicated at 40) of staples 5 and a sinuous staple advancing spring 41.

The bottom end of the staple feeding track 37 is defined by a shoulder 42 having the same configuration as the underside of portions 6, 7a and 8a of staple 5 (FIG. 2). The shoulder 42 is flanked by a pair of clearance notches 43 and 44 which are, in turn, flanked by shoulders 45 and 46, respectively. The bottommost end of the staple housing is provided with a notch 47 (larger than the notch 22 of the staple former housing 14 to permit a formed staple to be removed from the anvil 4) constituting a part of notch 3 of FIG. 1.

A divider wall 48 is shown in FIG. 4 and comprises a substantially rectangular, planar element. The lowermost end of divider wall 48 is provided with a pair of notches 49 and 50 defining bottom edge surfaces 51, 52 and 53.

Divider wall 48 is intended to separate the staple feeding track 37 from the staple forming track 24. To this end, the divider wall 48 is so sized as to be supported on shoulders 38 and 39 of the staple housing. When the staple former housing 14 and staple housing 15 are mated, staple former housing surface 23 will lie in abutting relationship with staple housing surface 36 and will overlap and maintain in place the divider wall 48. The shoulder 17 of staple former housing 14 will lie in abutment with shoulder 34 of staple housing 15, the shoulder 17 forming the upper end of the staple feeding track 37. The upper end 54 of the divider wall 48 will lie in abutment against shoulder 17 of the staple former housing 14. The bottom end edges 51 and 52 of divider wall 48 will contact shoulders 45 and 46, respectively of the staple housing 15. It will be understood that in the assembly thus far described, when the stack of staples 40 and the sinuous spring 41 are located in place within the staple feeding track 37, the uppermost end 41a of the sinuous spring will abut the shoulder 17 of the staple former housing 14 and the lower end 41b of sinuous spring 41 will engage the uppermost staple of the stack 40. The shoulder 42 of the staple housing and lower edge 53 and notches 49 and 50 of divider wall 48 are, when the cartridge is assembled, separated from each other by a distance slightly greater than the thickness of one staple. In this way, the shoulder 42 of the staple housing and the lower end of divider wall 48 form a horizontal passage or "window" through which the lowermost staple of stack 40 may pass from staple feeding track 37 to staple forming track 24 under the urging of a positive horizontal feeder to be described hereinafter. This window is shown at 55 in FIGS. 6 through 9.

The horizontal feeder housing 16 is illustrated in perspective in FIG. 4 and comprises an elongated substantially rectangular element. The exterior surface 56 of the horizontal feeder housing 16 is substantially planar, as shown in FIG. 6. The interior surface 57 is also substantially planar having a longitudinally extending depression 58 therein and a U-shaped opening 59 defining an integral, resiliently biased tine, hereinafter referred to as the horizontal feeder 60.

Horizontal feeder 60 has a normally planar portion 61 which constitutes a continuation of the bottom surface of depression 58. The planar portion 61 terminates in a wedge-shaped cam surface 62 and a pusher portion 63 the forward edge 63a of which corresponds in shape to portions 6, 7a and 8a of staple 5 (see FIG. 2). It will be understood that the staple housing 15 has, adjacent shoulder 42, an opening therein permitting the pusher portion 63 of the horizontal feeder to be freely shifted therethrough. This opening is most clearly shown in FIG. 14 at 64. Finally, the horizontal feeder housing 16 has at its lowermost end a notch 16a constituting a part of notch 3 of FIG. 1.

FIG. 4 illustrates a horizontal feeder activator 65. Activator 65 comprises an elongated element terminating in a rounded nose 66 at one end and a driving eyelet 67 at the other. Activator 65 is adapted to lie in and be reciprocable in channel 58 of horizontal feeder housing 16. Driving eyelet 67 extends through the notch 35 in the upper end of the staple housing 15 and through the elongated opening 18 in the staple former housing 14, to be engaged by a drive pin of the surgical stapling instrument 9. The drive pin is illustrated in broken lines at 68 in FIGS. 6 through 9.

FIGS. 6 through 13 illustrate the staple cartridge and feed means of the present invention in its fully assembled form and they further illustrate its operation. Turning first to FIGS. 6 and 10, the staple cartridge and feed means is shown in its normal, at rest condition, mounted upon the surgical stapling instrument 9 (not shown). The manner in which the cartridge is held in place on the surgical stapling instrument 9 does not constitute a part of this invention. The surgical stapling instrument anvil 4 is shown in broken lines located within the notch 3 in the end of the cartridge 1. The drive pins 29 and 68 of the surgical stapling instrument 9 are shown located within driving eyelets 25a of staple former 25 and driving eyelet 67 of horizontal feed activator 65, respectively.

Initially, the staple former 25 is in its fully retracted position and is maintained there by the staple former detainer tine 21 of staple former housing 14. A primary purpose of staple former detainer line 21 is to assure that the staple former 25 remains in its fully retracted position during shipping and handling. This, in turn, assures that staple former 25 will be in proper position to receive drive pin 29 during attachment of the cartridge 1 to the surgical stapling instrument 9. The staple former detainer tine 21 also serves to hold staple former 25 in its uppermost position during the lost motion sequence of drive pin 29.

It will be noted that the horizontal feeder activator 65 is normally in its fully retracted position. As a consequence, when the resiliently biased horizontal feeder 60 is in its normal position, the pusher portion 63 thereof extends through opening 64 in staple housing 15, beneath the lowermost staple 5a of stack 40 and into window 55 with the forwardmost edge 63a of pusher portion 63 being coplanar with that surface of divider wall 48 adjacent staple former 25. This effectively closes window 55 assuring that none of the staples of the stack 40 passes therethrough. Finally, in the normal at rest position of the cartridge 1, staple retainer springs 27 and 27a abut divider wall 48 and staple housing 15 at the region of window 55, forming another effective closure for the window. This is illustrated in FIG. 10 and particularly in FIG. 6 wherein spring 27a is shown.

Turning to FIGS. 7 and 11, as the trigger 13 of surgical stapling instrument 9 (FIG. 3) is actuated, drive pins 29 and 68 of the surgical stapling instrument 9 are driven toward the forming anvil 4. Initial movement of drive pin 29 does not move staple former 25 since, as can be noted from FIG. 7, the diameter of driving eyelet 25a of staple former 25 is larger than the diameter of the stapling instrument drive pin 29. Staple former detainer tine 21 retains staple former 25 in its uppermost position.

Driving eyelet 67 of the horizontal feeder actuator 65 has an internal diameter so sized as to just receive surgical stapling instrument drive pin 68. As a consequence, initial movement of drive pin 68 will cause the horizontal feeder activator 65 to shift downwardly. Rounded nose 66 of the horizontal feeder activator 65 engages cam surface 62 of the horizontal feeder 60 causing the feeder 60 to be deflected from its normal position and withdrawing pusher portion 63 of the horizontal feeder from window 55 and staple feeding track 37. This, in turn, permits the stack of staples 40, under the influence of sinuous spring 41, to shift vertically downwardly until the lowermost staple 5a of the stack 40 abuts shoulder 42 of staple housing 15. The bottommost staple 5a of stack 40 is prevented from passing through window 55 by staple retainer springs 27 and 27a. It will be noted in FIG. 7 that at this stage of the staple cartridge and feed means cycle the surgical stapling instrument drive pin 29 has contacted driving eyelet 25a of staple former 25 and is about to begin downward movement of staple former 25.

The next stage of the staple cartridge and feed means cycle is illustrated in FIGS. 8 and 12. Once the components of the staple cartridge and feed means have reached their positions illustrated in FIG. 7, it will be noted from FIG. 8 that the direction of drive pin 68 is rapidly reversed, quickly returning the horizontal feeder activator 65 to its normal position. This causes resiliently biased horizontal feeder 60 to return to its normal position. During the return of the resiliently biased horizontal feeder 60 to its normal position, its pusher portion 63 passes through staple feeding track 37 stripping the bottommost staple 5a from staple stack 40 and transferring the bottommost staple 5a horizontally through window 55 and into staple forming track 24. As will be evident from FIG. 8, the movement of lowermost staple 5a into staple forming track 24 under the influence of pusher portion 63 of horizontal feeder 60 results in a slight deflection of staple retainer springs 27 and 27a into the depression 26 of the staple former housing 14. Staple retainer springs 27 and 27a cooperate with pusher portion 63 of horizontal feeder 60 to maintain staple 5a in a position part way within staple forming track 24. It will further be noted from FIGS. 8 and 12 that staple former 25 has begun its downward movement past staple former detainer tine 21 under the influence of the surgical stapling instrument drive pin 29. Retainer springs 27 and 27a bias the staple 5a against pusher portion 63. Staple former 25 pushes springs 27 and 27a into depression 26 while horizontal feeder 60 urges staple 5a fully into forming track 24. Thus it will be noted from FIGS. 8 and 12 that at this stage of the staple cartridge and feed means cycle a single staple 5a has been selectively moved from the bottom of the stack of staples 40 into a position within staple forming track 24 below the staple former 25 where it is ready to be formed by the staple former about surgical stapling instrument anvil 4. The staple feeding portion of the cartridge cycle has been accomplished and the staple forming portion of the cycle is ready to begin.

Continued motion of surgical stapling instrument drive pin 29 will cause staple 5a and thereafter staple former 25 to contact staple ejection spring legs 28d and 28e. The slight downward slope of these legs (see FIG. 15) will cause them and tabs 28f and 28g to be bent away from the free end of anvil 4 to a retracted position out of staple former track 24. Further downward motion of the staple former will implant staple 5a in the skin or fascia of the patient and form the staple about the surgical stapling instrument anvil 4. At this point, the components of the staple cartridge and feed means will be in the positions shown in FIGS. 9 and 13 with staple former 25 maintaining staple ejection spring 28 in its retracted position. As will be evident from FIG. 13, the relieved edges 31 and 32 of staple former 25 will ease the crown 6 of staple 5a into the staple former notch 30 causing a bending of portions 7a and 8a of staple 5a until staple 5a assumes the configuration illustrated in FIG. 13.

Release of trigger 13 of the surgical stapling instrument 9 will result in the return of drive pin 29 to its normal position, returning staple former 25 to its uppermost position. This, in turn, will free staple ejection spring 28 to return to its normal position. In so doing, staple ejection spring tabs 28f and 28g will contact formed staple 5a near the center of its crown and push the staple off of anvil 4. It will be understood that when staple ejection spring is held in its retracted position (FIG. 9), the sides 28b and 28c thereof will be twisted in torsion spring fashion so that they will tend to urge tabs 28f and 28g to their normal positions. Once staple 5a is removed from anvil 4, all of the components of the staple cartridge and feed means will then be in their normal, at rest positions illustrated in FIG. 6 and the cycle can thereafter be repeated.

As applied herein and in the claims, the terms "vertical" and "horizontal" are used simply to define the relative positions of the components of the staple cartridge 1 and its feed means. During use, it will be understood by one skilled in the art that the surgical stapling instrument 9 and cartridge 1 are likely to assume various positions wherein the staple feeding track 37 and the staple forming track 24 are not vertically oriented and the passage formed by window 55 is not horizontally oriented. Nevertheless, the relative orientations of these elements with respect to each other do not change.

Modifications may be made in the invention without departing from the spirit of it.

The embodiments of the invention in which an exclusive property or privilege is claimed are defined as follows:

1. A staple cartridge for use with a stapling instrument, said cartridge comprising a body having therein a staple forming track with a reciprocable staple former therein actuable by said instrument, a separate and distinct parallel staple feeding track for a stack of staples, a passage between said staple feeding and forming tracks so sized as to permit the passage therethrough of one staple at a time from said staple feeding track to said staple forming track, means actuable by said instrument to shift one staple at a time from said staple feeding track through said passage into said staple forming track, said staple shifting means closing said passage when a staple is not being shifted therethrough by said staple shifting means, and means to maintain a staple shifted into said staple forming track in proper position therein to be acted upon by said staple former.

2. The structure claimed in claim 1 including means separate and distinct from said staple shifting means to urge the bottommost staple of a stack thereof in said staple feeding track into position to be shifted through said passage by said staple shifting means.

3. A staple cartridge for use with and affixable to a surgical stapling instrument of the type having an anvil about which a staple is formed during emplacement thereof in the skin or fascia of a patient, said cartridge comprising a body having therewithin a vertical staple feeding track with closed upper and lower ends and a separate, parallel, vertical staple forming track with a closed upper end and an open lower end adapted to be adjacent said surgical stapling instrument anvil when said cartridge is affixed to said instrument, a staple former shiftable within said staple forming track by said instrument between a retracted position and an extended position wherein it forms a staple about said anvil, a stack of staples located within said vertical staple feeding track, a horizontal passage extending laterally from said vertical staple feeding track adjacent said lower end thereof to said vertical staple forming track and being so sized as to permit the shifting therethrough of only one staple at a time from said vertical staple feeding track to said vertical staple forming track, horizontal feeder means actuable by said instrument to shift the bottommost staple of said stack from said staple feeding track horizontally through said passage into said vertical staple forming track, said horizontal feeder means closing said passage when a staple is not being shifted therethrough by said horizontal feeder means and means to maintain a staple shifted into said vertical staple forming track in proper position therein to be engaged by said staple former and formed about said instrument anvil when said staple former is shifted by said instrument from said retracted to said extended position.

4. The structure claimed in claim 3 including staple ejection spring means within said staple cartridge to push a formed staple off of said anvil.

5. The structure claimed in claim 4 wherein said staple ejection spring means has a pair of legs normally extending across said staple forming track and having downwardly depending tabs normally lying just above said anvil at the free end thereof, said staple ejection spring legs and tabs being shiftable to a retracted position out of said staple forming track by a staple and said staple former during a staple forming operation whereby said staple ejection spring legs and tabs will spring back to their normal position upon formation of said staple and return of said staple former to said retracted position removing said formed staple from said anvil.

6. The structure claimed in claim 3 including means separate and distinct from said horizontal feeder means within said staple feeding track to urge said stack of staples toward said lower end of said staple feeding track.

7. The structure claimed in claim 6 wherein said means to urge said stack of staples toward said lower end of said staple feeding track comprises a sinuous spring the upper end of which abuts said closed upper end of said staple feeding track and the lower end of which abuts said stack of staples.

8. The structure claimed in claim 3 wherein said body is made up of three elements joined together in face-toface abutting relationship, said elements comprising a staple former housing, a horizontal feeder housing and an intermediate staple housing, said staple formed housing comprising an elongated substantially rectangular element having on its side facing said staple housing a longitudinally extending depression comprising said staple forming track, said intermediate staple housing comprising a substantially rectangular element having on its side facing said staple former housing a longitudinally extending depression comprising said staple feeding track and terminating at one end in a shoulder on said staple housing forming said lower end of said staple track, a thin, substantially rectangular divider wall mounted on said staple housing and separating said staple feeding track from said staple forming track when said staple housing and said staple former housing are joined together in said abutting relationship, said divider wall having a lower edge so configured and so spaced from said staple housing shoulder as to define therewith said horizontal passage, said staple housing having a transverse opening therein opposite said passage, said horizontal feeder housing comprising a substantially rectangular element having a longitudinally extending resilient tine comprising said horizontal feeder, said horizontal feeder having a free end terminating in a laterally extending pusher portion freely receivable through said opening in said staple housing when said staple housing and said horizontal feeder housing are joined together in said abutting relationship, said horizontal feeder being shiftable between a normal position wherein said pusher portion extends through said opening in said staple housing, through said staple feeding track and into said passage and a retracted position wherein said pusher portion is withdrawn from said passage and said staple forming track.

9. The structure claimed in claim 8 wherein said staple former housing, said horizontal feeder housing and said intermediate staple housing are removably joined together whereby said staple cartridge is refillable and reusable.

10. The structure claimed in claim 9 wherein said staple former housing, said horizontal feeder housing and said intermediate staple housing are made of stainless steel.

11. The structure claimed in claim 8 wherein said cartridge is disposable, said staple former housing, said horizontal feeder housing and said intermediate staple housing being permanently joined together.

12. The structure claimed in claim 11 wherein said staple former housing, said horizontal feeder housing and said intermediate staple housing are formed of plastic material.

13. The structure claimed in claim 8 including a pair of staple retainer springs, said staple former housing having a depression within said staple former track, said retainer springs being affixed at on end to said staple former housing within said depression, said retainer springs having a normal position wherein their free ends extend across said staple former track and abut said divider wall and staple housing spanning and additionally closing said passage, said retainer springs being partially deformable by a staple entering said staple former track under the influence of said pusher portion of said horizontal feeder and further deformable to a position wholly within said retainer spring depression by said staple former, said means to retain a staple in proper position within said staple former track comprising said retainer springs and said pusher portion of said horizontal feeder.

14. The structure claimed in claim 8 including an integral, resilient detainer tine on said staple former housing to normally engage and retain said staple former in its retracted position.

15. The structure claimed in claim 8 including a longitudinal channel in that side of said horizontal feeder housing facing said staple housing, a horizontal feeder actuator slidably mounted in said channel, said actuator comprising an elongated member having an upper end and a lower end, said horizontal feeder having a cam surface thereon, said actuator being vertically shiftable within said horizontal feeder housing channel by said instrument between a normal retracted position and an extended position wherein said lower end of said actuator engages said cam surface on said horizontal feeder to shift said horizontal feeder to said retracted position thereof.

16. The structure claimed in claim 15 wherein said actuator has at said upper end an integral laterally extending driving eyelet, said eyelet extending through a notch in said staple housing and an elongated hole in said staple former housing whereby said actuator driving eyelet may be engaged by a vertically shiftable drive pin of said surgical stapling instrument.

17. The structure claimed in claim 8 wherein said staple former has an integral laterally extending driving eyelet, said eyelet extending through an elongated hole in said staple former housing whereby said staple former driving eyelet may be engaged by a vertically shiftable drive pin of said surgical stapling instrument.

* * * * *